(12) United States Patent
Dooley

(10) Patent No.: US 8,095,324 B2
(45) Date of Patent: Jan. 10, 2012

(54) PERMANENT MAGNET ROTOR CRACK DETECTION

(75) Inventor: Kevin A. Dooley, Mississauga (CA)

(73) Assignee: Pratt & Whitney Canada Corp., Longueuil, Quebec (CA)

( * ) Notice: Subject to any disclaimer, the term of this patent is extended or adjusted under 35 U.S.C. 154(b) by 366 days.

(21) Appl. No.: 12/146,606

(22) Filed: Jun. 26, 2008

(65) Prior Publication Data

US 2009/0322373 A1    Dec. 31, 2009

(51) Int. Cl.
*G01B 5/28* (2006.01)

(52) U.S. Cl. ......................................... 702/35
(58) Field of Classification Search ............ 702/35
See application file for complete search history.

(56) References Cited

U.S. PATENT DOCUMENTS

| | | |
|---|---|---|
| 3,573,520 A | 4/1971 | Dorshimer |
| 4,026,660 A | 5/1977 | Ueda et al. |
| 4,134,067 A | 1/1979 | Woodbury |
| 4,808,932 A | 2/1989 | Schulz, Jr. et al. |
| 5,432,444 A | 7/1995 | Yasohama et al. |
| 5,442,285 A | 8/1995 | Zombo et al. |
| 5,510,709 A | 4/1996 | Hurley et al. |
| 5,554,933 A | 9/1996 | Logue |
| 5,648,721 A | 7/1997 | Wincheski et al. |
| 5,952,836 A | 9/1999 | Haake |
| 6,607,354 B1 | 8/2003 | Klapatch et al. |
| 6,756,908 B2 | 6/2004 | Gass et al. |
| 6,888,346 B2 | 5/2005 | Wincheski et al. |
| 6,949,922 B2 | 9/2005 | Twerdochlib et al. |
| 7,098,655 B2 | 8/2006 | Yamada et al. |
| 7,626,383 B1 * | 12/2009 | Sun et al. ................ 324/240 |
| 2002/0130659 A1 * | 9/2002 | Wincheski et al. ........ 324/235 |
| 2003/0051928 A1 | 3/2003 | Raftari et al. |
| 2003/0055584 A1 | 3/2003 | Raftari et al. |

OTHER PUBLICATIONS

Sharatchandra Singh W, et al "Detection of leakage magnetic flux from near-side and far-side defects in carbon steel plates using a giant magneto-resistive sensor: Detection of leakage magnetic flux from near-side and far-side defects in carbon steel plates" Measurement Science and Technology, IOP, Briston, GB, vol. 19, No. 1, Jan. 1, 2008, p. 15702, XP020129380, ISSN: 0957-0233.
European Search Report dated Feb. 15, 2011 issued by the European Patent Office with respect to Applicant's corresponding European application No. EP 09250875.3-1240/2138836.

* cited by examiner

*Primary Examiner* — Aditya Bhat
(74) *Attorney, Agent, or Firm* — Norton Rose Or LLP

(57) ABSTRACT

A method and apparatus for permanent magnetic (PM) rotor crack detection includes a sensor which monitors magnetic flux distribution of the PM rotor and identifies the presence of a crack in the PM rotor when a magnetic flux distribution change or anomaly is detected.

20 Claims, 3 Drawing Sheets

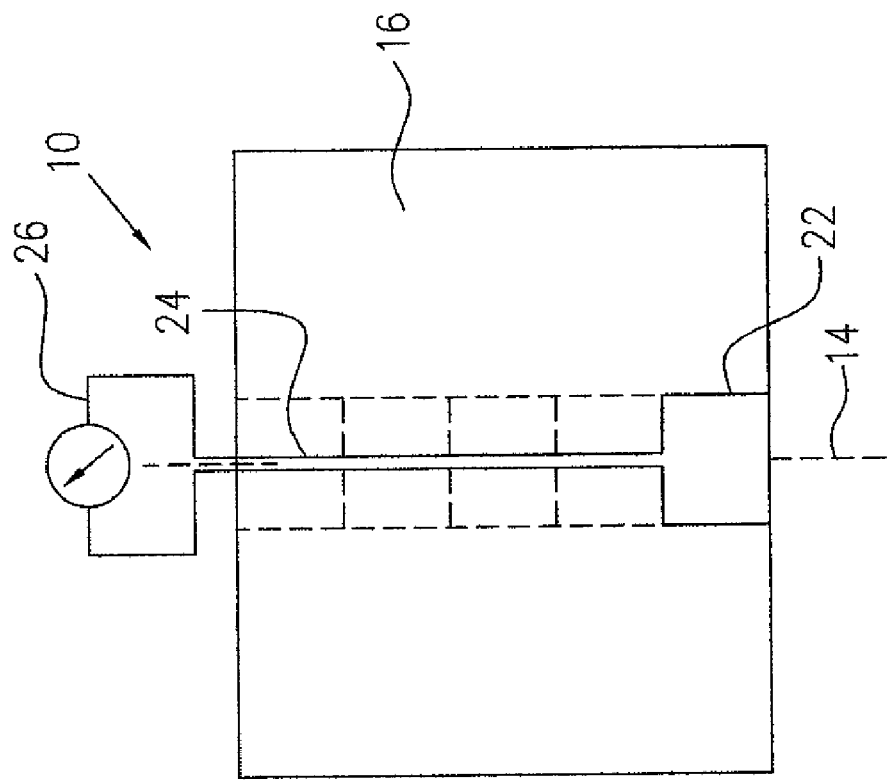
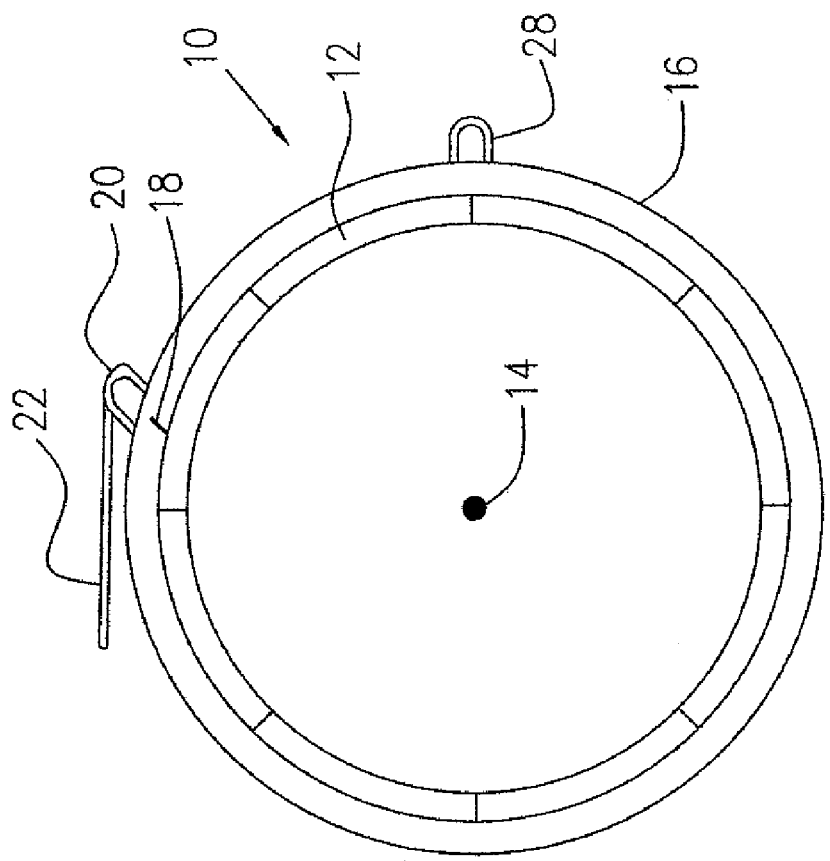

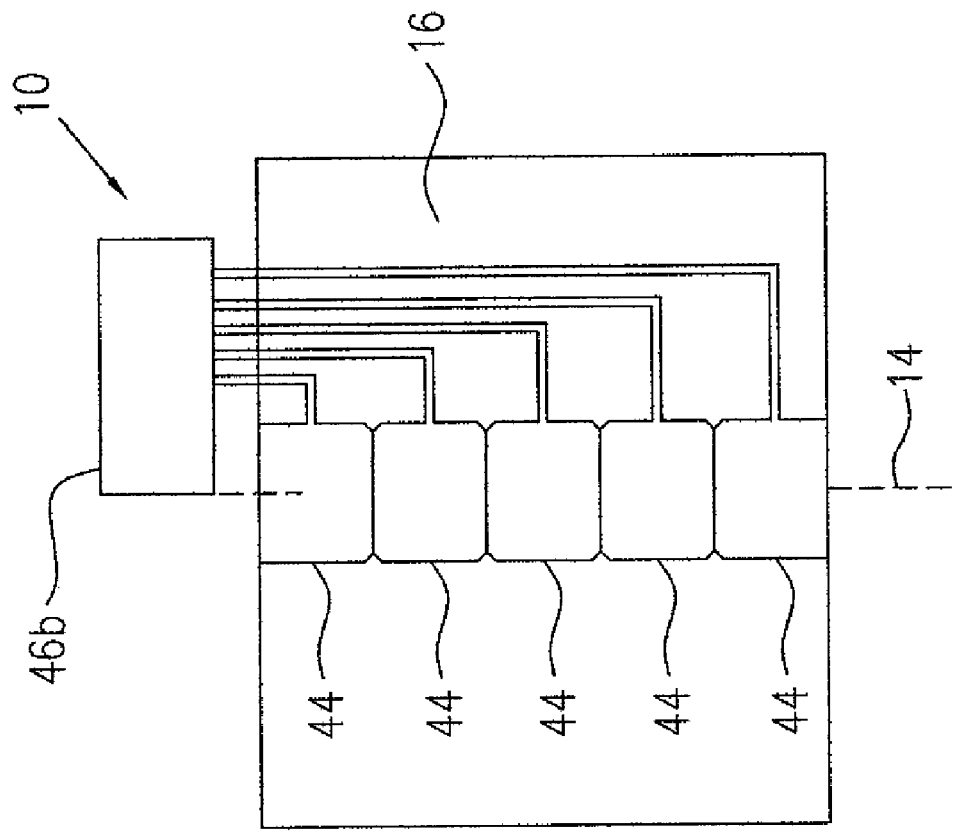
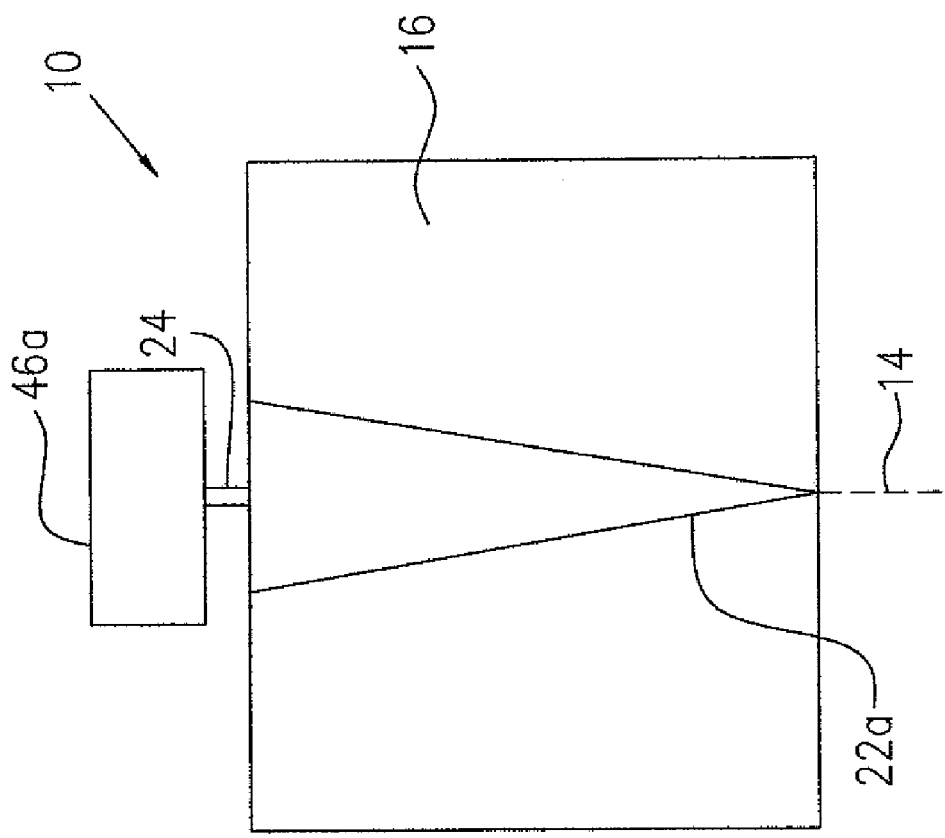
FIG. 5
FIG. 4

PERMANENT MAGNET ROTOR CRACK DETECTION

TECHNICAL FIELD

The technique relates generally to permanent magnetic rotors and, more particularly, to an improved method and apparatus for permanent magnetic rotor crack detection.

BACKGROUND OF THE ART

As a safety issue, permanent magnetic (PM) motors/generators must be properly maintained. Any cracks developed in the PM rotors over time must be identified at an early stage in crack development. Although crack inspection devices are known and can be used to detect cracks in rotors, such inspections are usually only available when the rotors are not in operation and the inspection procedure may require the rotor to be disassembled from the rotor machine.

Accordingly, there is a need to provide an improved technique and apparatus for permanent magnetic rotor crack detection.

SUMMARY OF THE DESCRIPTION

In one aspect, the description provides a method for permanent magnetic rotor in situ crack detection which comprises (a) positioning a sensor in a first location adjacent a permanent magnetic rotor, the sensor being adapted for sensing a magnetic flux distribution of the permanent magnetic rotor when the rotor rotates; b) monitoring the magnetic flux distribution of the permanent magnetic rotor in said location during a rotor operation; c) identifying the presence a crack in the permanent magnetic rotor when an unknown magnetic flux distribution anomaly of the rotor is detected.

In another aspect, the description provides a method for permanent magnetic rotor in situ crack detection which comprises (a) positioning a wire loop in a first location adjacent a permanent magnetic rotor, the wire loop being connected to an electric circuit for sensing a magnetic flux distribution of the permanent magnetic rotor when the rotor rotates; (b) monitoring the magnetic flux distribution of the permanent magnetic rotor in said location during a rotor operation; and (c) identifying the presence of a crack in the permanent magnetic rotor when an unknown magnetic flux distribution anomaly of the rotor is detected.

In a further aspect, the description provides an apparatus for permanent magnetic rotor in situ crack detection which comprises a wire loop adapted to be placed adjacent a permanent magnetic rotor, a device connected to the wire loop for receiving electric current/voltage signals generated by the wire loop in every rotation cycle of the permanent magnetic rotor when the rotor rotates, the device including a memory element recording the electric current/voltage signals generated by the wire loop, and a software which compares a currently received electric current/voltage signal in an instant rotation cycle of the permanent magnetic rotor with a selected one of the recorded electric current/voltage signals, said selected signal representing a magnetic flux distribution of the permanent magnetic rotor without a crack, and which sends an alarm signal of the presence of a crack in the rotor when a substantial difference between the compared signals is identified.

Further details of these and other aspects of the technique will be apparent from the detailed description and figures included below.

DESCRIPTION OF THE DRAWINGS

Reference is now made to the accompanying figures depicting aspects of the technique, in which:

FIG. 1 is a schematic cross-sectional view of a permanent magnetic rotor in rotation which is monitored by a sensor to detect cracks developed in the rotor, according to one embodiment;

FIG. 2 is a schematic top plane view of the permanent magnetic rotor of FIG. 1, in rotation, illustrating an axial position of the sensor with respect to the rotor;

FIG. 4 is a schematic top plane view of the permanent magnetic rotor of FIG. 1, in rotation, illustrating a triangular loop sensor, according to another embodiment; and FIG. 5 is a schematic top plane view of the permanent magnetic rotor of FIG. 1, in rotation, illustrating a plurality of sensors in a series of axial locations with respect to the rotor, according to another embodiment.

DETAILED DESCRIPTION

Figure 3:
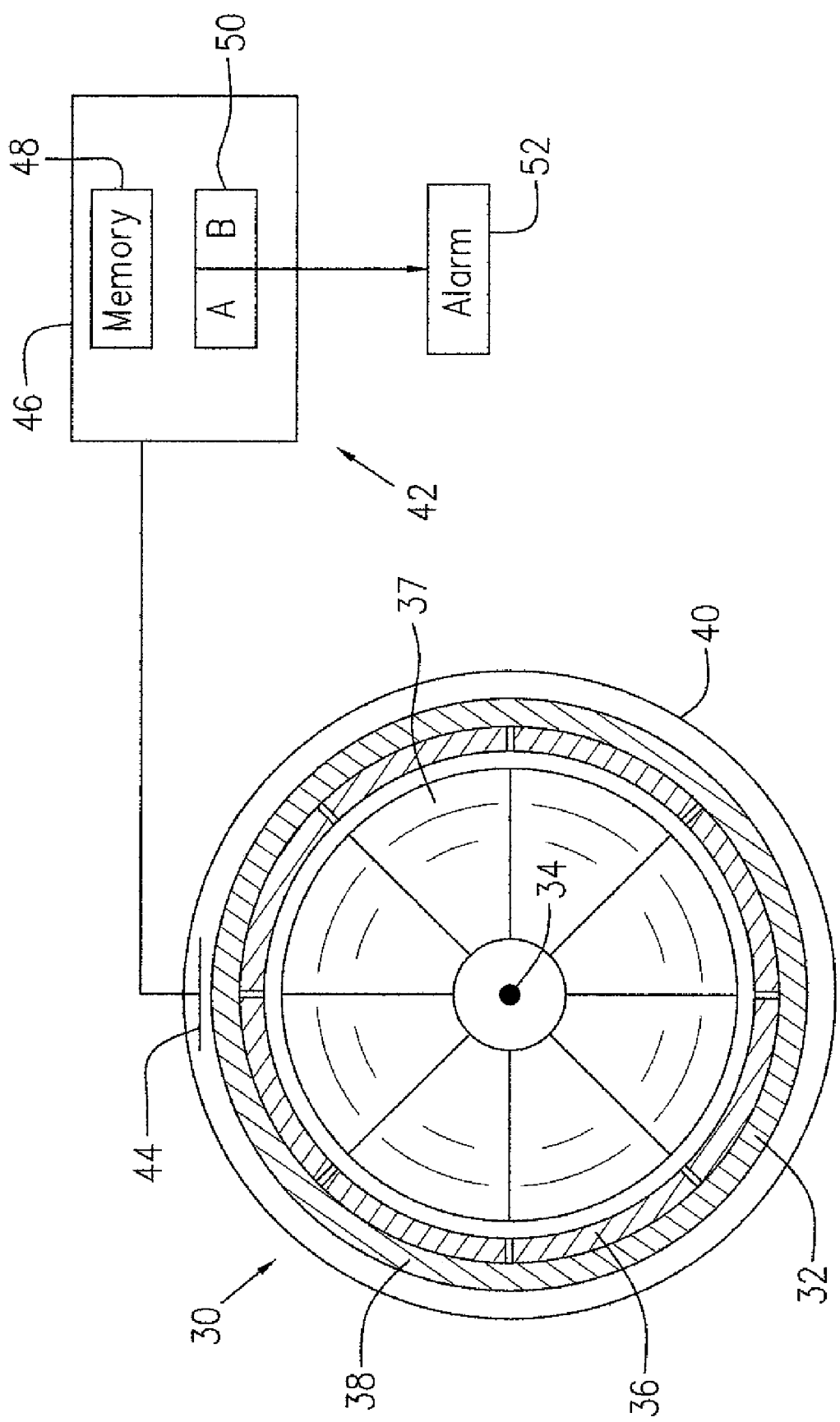
FIG. 3 is a schematic illustration of a permanent magnetic rotor machine in a cross-sectional view and a block illustration of the apparatus used to detect cracks developed in the rotor of the permanent magnetic rotor machine, according to another embodiment.

In FIGS. 1 and 2, a method for permanent magnetic rotor crack detection is illustrated. A permanent magnetic rotor 10 which is widely used in permanent magnetic rotor machines such as permanent magnetic rotors/generators in gas turbine engines or used in other technical fields, generally includes a plurality of magnets 12 positioned to form a circumferential array, as shown in FIG. 1. When the rotor 10 rotates about a rotational axis 14, the magnetic flux field provided by the array of magnets 12 rotates with the rotor 10, and causes induction current in stator windings (not shown) which may be radially spaced apart but adjacent the rotor 10 in a radial gap machine (located either inside or outside the machine) or axially spaced apart but adjacent the rotor 10 in an axial gap machine. This is a general operating principle of a permanent magnetic generator. When working as a permanent magnetic motor, the rotor 10 is driven to rotate about axis 14 due to the interaction between an alternating electric field produced by the stator windings adjacent the rotor 10 (either in a radial gap machine or in an axial gap machine) and the magnetic field of the permanent magnetic rotor 10.

The magnetic steel structure of a permanent magnetic rotor, particularly an outside permanent magnetic rotor which is positioned radially outwardly of a coaxial stator (which will be further described with reference to FIG. 3 below), includes a steel ring 16 in order to provide structural support to the magnets 12 and the rotor 10. The steel ring 16 also conducts magnetic flux as part of the magnetic circuit. Over time due to stress cycles it is possible for cracks to occur and develop in the highly stressed steel support structure of the rotor 10, which is an indication of impending failure of the rotor structure. Therefore, early detection of cracks in the rotor is desired in order to avoid failure of the rotor structure. Because the steel support structure is also carrying magnetic flux, a crack, for example as indicated by numeral 18, which presents as a magnetic discontinuity in the material of the steel supportive structure 12, will result in a measurable change or anomaly(ies) in the magnetic flux leakage (indicated by numeral 20) in the vicinity of the crack 18. When a magnetic flux detector or sensor 44 (as shown in FIG. 3) in this example comprising a circuit including an electrically simple conductive wire loop 22 and a current/voltage monitor 26, is positioned in a location adjacent the rotor 10, changes in surface flux leakage such as the magnetic flux leakage or anomaly 20 can be detected. The flux leakage or anomaly 20 in motion, due to the rotation of the rotor 10, will result in a current/voltage induced in the wire loop 22 when the location of the crack 18 and thus the magnetic flux leakage or anomaly 20, passes the wire of the wire loop during a normal operation of the rotor. The current/voltage amplitude induced in the wire loop 22 will be directly proportional to the amount of total flux leakage magnitude times the rotor speed. This permits tracking of the growth or propagation of such a crack over any number of cycles, and permits a prognostic prediction on remaining rotor life to be calculated, once the system has been calibrated, as well as health trending over time, etc. More detailed analysis of the signal from the sensor 44 may be undertaken, as well, to provide more information, such as relating to crack dimensions and the number of cracks (if there are more than one), etc.

The location of the crack 18 in the rotor 10 can also be identified if required using the sensor 44 in close proximity to only certain portions of the rotor, wherein the crack's location may be localized, as will now be described. As illustrated in FIG. 2, the wire loop 22 may be configured with an axial dimension of only a fraction of the entire axial length of the rotor 10 (about $1/5^{th}$ of the length of the rotor, for the example shown in FIG. 2), and with a wire portion 24 wherein the two halves of the circuit are in close proximity to one another. During a permanent magnetic rotor crack detection operation, the wire loop 22 is, for example, first located near one axial end of the rotor 10 and then the rotor is rotated. If a crack in the rotor 10 is detected, then it can be determined that this crack must be present within this first axial section near the end of the rotor 10. If a crack is present in a location other than in that axial section of the rotor, the magnetic flux leakage caused by that crack will not pass the wire loop 22. Although the crack may pass the two wires 24 connecting the wire loop 22 to an electric circuit monitor 26, since the two wires 24 are positioned close together, any current/voltage induced in the two wires 24 by a magnetic flux leakage in motion will be in equal amounts but opposed directions/polarities in the electric circuit, thereby resulting in a zero input. In this way, only the loop portion 22 of the circuit is sensitive to cracks, and cracks detection within the rotor may therefore be localized to some extent. Therefore, the wire loop 22 can be successively repositioned axially along the rotor, as the rotor is rotated, so that a number of discrete axial sections, extending across the entire axial length of the rotor 10 as shown in broken lines in FIG. 2, may be inspected. The axial location of a crack in the rotor 22 can thereby be identified, or at least its location narrowed down on the rotor.

In one embodiment, a further refinement of this crack-locating feature is refined. Referring to FIG. 4, a wire loop 22a having a triangular type of shape, where the point of the triangle is located at one axial extreme of the rotor while the more separated portion (between the wires), is located at the other axial extreme of the rotor, such that a crack passing near to the pointed end (where the wires are close together) will cause a plus-minus pulse with little time between the plus and minus pulses, while a crack located at the other axial extreme would result in two separate pulses having a greater time between them. Timing the delay between initial pulse and the second, and taking the rotor speed into account could establish the exact position of a discrete crack established with a single loop of wire 22a. A crack which is initially at one axial location and then propagates in the axial direction will produce a signature which will change in a calculable way as the crack gets longer. The signals received by 22a are processed by device 46a.

The circumferential location of crack 18 may also be determined by acquiring rotor position information and analyzing it together with crack position information. For example, referring again to FIG. 1, the circumferential location of crack 18 may be determined simply, with respect to a reference mark 28 having a known location in the rotor 10, can be calculated if the reference mark 28 is also sensed when the crack 18 is detected. One example of the reference mark 28 according to this embodiment, is a known magnetic anomaly of the rotor 10 which has a known circumferential location. The known magnetic anomaly as the reference mark 28 will also be detected by the wire loop 22 in each rotation cycle of the rotor 10. The circumferential location of the crack 18 with respect to the reference mark 28 can thus be calculated on the basis of the rotor speed and the time difference between the detected crack 18 and the detected reference mark 28. The skilled reader will appreciate that rotor position information may be obtain in any suitable manner, such as using information obtained from a designated rotor position sensor, if present. Alternately, reference mark 28 may be of another type (i.e. not simply another magnetic anomaly) detected by another suitable type of sensor, e.g. optical sensor, etc. Many different types of sensor arrangements are known in the art for detecting rotational position and hence need not be further described herein.

This crack detection approach is applicable to any permanent magnetic rotor regardless of the type of rotor or machines, and may apply to axial gap rotor machines as well as radial gap rotor machines, outer rotor machines as well as inner rotor machines, and so on. The above description describes and illustrates some details of the principle of the permanent magnetic rotor crack detection, but is not intended to be limited to any structural features of the machine to which the crack detection operation is suitable.

FIG. 3 illustrates an apparatus used in a permanent magnetic rotor machine of an outer rotor type, according to an embodiment. Permanent magnetic rotor machine 30 includes an annular rotor 32 supported on a rotating shaft 34, which rotates together with shaft 34. The rotor 32 includes a circumferential array of permanent magnets 36 attached to the inside of a steel support ring 38. A stator 37 is positioned between the rotor 32 and the rotating shaft 34, coaxially therewith, and is supported by a stationary structure (not shown) of the machine 30. The stator 37 includes a plurality of windings (not shown). A stationary casing 40 of aluminium or other metal material, surrounds the rotor 32.

An apparatus 42 for permanent magnetic rotor in situ crack detection within the machine, includes in this example a sensor 44 which is adapted to send electric current/voltage signals when sensing magnetic flux distribution changes, for example, detection of the magnetic flux leakage or anomaly passing thereby. The sensor 44 is placed adjacent the rotor 32 and may be positioned in an air gap between an outer surface of the permanent magnetic rotor 32 and an inner surface of the stationary casing 40 for crack detection operation. (Crack detection operation of the apparatus should not be affected by the stationary casing 40, regardless of the materials of the casing 40 which is ferrous or non-ferrous metal.) The apparatus 42 includes a device 46 connected to the sensor 44 for receiving the electric current/voltage signals generated by the sensor 44. Operation of the apparatus 42 is generally as described above, with reference to FIG. 1.

The device 46 further includes a memory element 48 which records the signals received from the sensor 44. A software 50 of the device 46 is adapted for comparing a present signal to a signal from a previous rotation cycle(s) of the rotor recorded in the memory element 48. In one example, the signal recorded in the memory element 48 represents a "normal" rotor—i.e. one with a magnetic flux distribution of the rotor 32 without any cracks in normal operation. The software 50 sends an alarm signal of the presence of a crack in the rotor 32 when a substantial change between the compared signals is identified. (This comparing function of the software 50 is indicated by letter A in FIG. 3.) In another example, the present signal may be compared with a signal measurement from previous rotation cycle(s), and the result of such a progressive comparison may be used to track/show the development or progression of a crack in the rotor 32, once initiated and identified.

In another example, the software 50 may calculate (B in FIG. 3) the circumferential position of the identified crack with respect to a known magnetic anomaly in the rotor 32 or other rotor position information, as discussed above. An alarm member 52 may also be included in the apparatus 42 which may be any suitable alarm, such as a sound alarm device and a visual display to show the comparison result of function A and the circumferential position of the crack with respect to the known magnetic anomaly in the rotor 32, as calculated by the function B in the software 50. In another example, the alarm may comprise setting a logic flag or issuing a fault code which may be sent to, or retrieved by, those responsible for machine maintenance, and/or to a machine health monitoring database. Although an on-board memory device and on-board comparator is described, it will be understood that data may be communicated to a remote or central site, where such comparing, monitoring, alarming, etc. may be conducted/managed.

In another example, the software is adapted to calculate the axial position of a crack by the application of a triangular shaped wire loop 22a, and included in the processing device 46a as described above with reference to FIG. 4.

Sensor 44 may be a wire loop 22 similar to that described with reference to FIG. 1 and or may be a Hall Effect device or a Giant Magnetoresistance Device (GMR) to sense magnetic fields.

As shown in FIG. 5, a plurality of sensors 44 may be provided along an axial length of the rotor, to allow multiple crack detection readings to be made in parallel and processed by processing device 46b. This may be used, for example, to facilitate axial positioning of a crack anomaly, rather than the serial method described with respect to FIG. 2 above.

The above description is meant to be exemplary only, and one skilled in the art will recognize that changes may be made to the embodiments described without departure from the technique description. Modifications will be apparent to those skilled in the art, in light of a review of this disclosure, and such modifications are intended to fall within the appended claims.

The invention claimed is:

1. A method for detecting cracks in a permanent magnetic rotor of an electric motor/generator, comprising:
   a) providing an apparatus for sensing a magnetic flux field in motion;
   b) using said apparatus to sense a magnetic flux distribution of a magnetic flux field of the permanent magnetic rotor when the magnetic flux field rotates together with the rotor;
   c) using the apparatus to monitor the magnetic flux distribution of the magnetic flux field of the permanent magnetic rotor;
   d) detecting an anomaly in the magnetic flux distribution using the apparatus, the anomaly associated with a location on the permanent magnetic rotor;
   e) identifying a crack location on the permanent magnetic rotor associated with said rotor location.

2. The method as defined in claim 1 wherein the crack location includes at least one of a rotor circumferential position and a rotor axial position of said crack.

3. The method as defined in claim 1 comprising determining an axial position of the anomaly on the rotor by confining said step of detecting to a selected first axial section of the rotor and then performing said step of detecting on other axial sections of the rotor until an anomaly is detected, the axial section within which the anomaly was detected being associated with a rotor axial position of the crack.

4. The method as defined in claim 3 wherein the selected axial sections are polled serially successively by a magnetic flux distribution single sensor.

5. The method as defined in claim 3 wherein the apparatus includes a sensor positioned in a second location adjacent the permanent magnetic rotor, and then repeating steps (c) and (d), the second location being axially adjacent the first location with respect to an axial length of the permanent magnetic rotor.

6. The method as defined in claim 5 comprising repeating steps (b), (c) and (d) until discrete locations in which the sensor has been positioned extend across the axial length of the permanent magnetic rotor.

7. The method as defined in claim 1 wherein the anomaly is detected by comparing a measured magnetic flux distribution with a reference magnetic flux distribution.

8. The method as defined in claim 7 wherein the reference magnetic flux distribution is a previously recorded measurement associated with a crack-free rotor.

9. The method as defined in claim 1 further comprising acquiring rotor position information and using said information to determine a circumferential position of the anomaly on the rotor.

10. The method as defined in claim 9 wherein the rotor position information is obtained by providing a marker on the rotor at a known circumferential location, detecting the marker on successive rotor revolutions, and comparing information on the marker position and crack anomaly to determine the circumferential position of the crack on the rotor.

11. The method as defined in claim 10 wherein detecting the marker is achieved by using the apparatus to sense a pulse signal associated with a known magnetic marker anomaly associated with the marker of the permanent magnetic rotor.

12. The method as defined in claim 1 wherein the step of detecting an anomaly is achieved by placing an electrically conductive wire adjacent permanent magnets of the rotor, the wire included in an electric circuit of the apparatus adapted to sense electricity in the circuit.

13. The method as defined in claim 1 wherein the step of detecting the anomaly is achieved by monitoring an output of a sensor of the apparatus, the sensor placed adjacent permanent magnets of the rotor, the sensor selected from the group consisting of a Hall Effect device and a Giant Magnetoreisistance device.

14. The method as defined in claim 1 comprising repeating the four steps over time to obtain crack trending information.

15. The method as defined in claim 14 further comprising providing the crack trend information to at least one of a machine operator and a machine maintenance personnel.

16. The method as defined in claim 1 further comprising the step of setting a warning upon detection of a crack.

17. A method for detecting cracks in a permanent magnetic rotor of an electric motor/generator, comprising:
  a) providing an apparatus including a wire loop for sensing a magnetic flux field in motion;
  b) positioning the wire loop in a selected location adjacent the permanent magnetic rotor, the wire loop being connected to an electric circuit of the apparatus for sensing a magnetic flux distribution of a magnetic flux field of the permanent magnetic rotor when the magnetic flux field rotates together with the rotor;
  c) monitoring the magnetic flux distribution of the magnetic flux field of the permanent magnetic rotor using the wire loop of the apparatus in said location during a rotor operation; and
  d) identifying the presence of a crack in the permanent magnetic rotor when an unknown magnetic flux distribution anomaly of the rotor is detected.

18. The method as defined in claim 17 wherein an electric signal associated with an instant rotation cycle of the permanent magnetic rotor is compared with a recorded electric signal associated with a previous rotation cycle of the permanent magnetic rotor.

19. An electric machine system comprising:
  a permanent magnetic rotor rotatably mounted adjacent a stator;
  means for detecting a crack in the permanent magnetic rotor during rotation, said means using a measured magnetic flux distribution of a magnetic flux field of the permanent magnetic rotor as the magnetic flux field rotates together with the rotor during normal operation of said electric machine system; and
  a computer system communicating with said means for recording information associated with a detected crack in the permanent magnetic rotor.

20. The electric machine system as defined in claim 19, wherein the means includes a sensor positioned in an air gap between the permanent magnetic rotor and a surface of a stationary housing of the electric machine system.

* * * * *